United States Patent [19]

Schwartz, deceased

[11] Plant 4,294

[45] Aug. 15, 1978

[54] ROSE PLANT

[75] Inventor: Ernest Schwartz, deceased, late of Kingsville, Md., by Hazel E. Schwartz, executrix

[73] Assignee: F. Harmon Saville Nor'East Miniature Roses, Rowley, Mass.

[21] Appl. No.: 854,514

[22] Filed: Nov. 25, 1977

[51] Int. Cl.[2] ..... A01H 5/00

[52] U.S. Cl. ..... Plt./9

[58] Field of Search ..... Plt./7, 9

*Primary Examiner*—Robert E. Bagwill
*Attorney, Agent, or Firm*—Vincent G. Gioia

[57] ABSTRACT

A novel rose variety of the miniature rose class characterized by high centered pink blooms, borne primarily one to a stem and with reflexing petals folding individually along the entire margin as they mature.

1 Drawing Figure

1

The present invention relates to a new and distinct variety of rose plant of the miniature rose class, which was originated by my crossing as seed parent a self seedling of the new rose known as "Gold Coin" and an unnamed seedling as pollen parent.

Among the novel characteristics possessed by this new variety which distinguish it from its parents and all other varieties of which I am aware are: (1) recurrent blooms of coral pink coloring, (2) high centered flowers borne primarily singly to a stem in a manner typical of hybrid tea plants opening flat but symmetrical, (3) petals reflexing individually along the entire margin as they mature and (4) a free-branching vigorous plant. Asexual reproduction by budding of the new variety as performed in Essex County, Mass., shows that the foregoing and other distinguishing characteristics come true to form and are established and transmitted through succeeding propagations.

The new and improved rose variety which I have developed is a miniature rose of coral pink coloring, with singly-borne blooms of high centered, hybrid-tea form delightfully displayed on a vigorous, free branching plant. The flowers usually have 28 to 35 petals but the petalage is increased with heavy fertilization. Despite this relatively heavy petalage, the blooms open well and hold their coloring under varied and adverse weather conditions. The plant itself is attractive in combining medium, abundant foliage with well branching growth.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "45B" is plate 45B of the Royal Horticultural Society Color Chart.

Parentage: Seedling.

*Seed parent.*—A self seedling of "Gold Coin".

*Pollen parent.*—"Unnamed seedling".

Class: Miniature.

2

The following observations are made of specimens grown outdoors with 30% shade in Essex County, Mass., during the month of October.

1. FLOWER

Blooming habit: Recurrent.

A. Bud:

(1) *Size.*—Medium.

(2) *Form.*—Short, pointed.

(3) *Color.*—When sepals first divide — 47A. When petals begin to unfurl — 39A. When half-blown: 39B. Reverse side of petals — 52C.

(4) *Sepals.*—Smooth, occasionally lightly foliated long, thin, tapered, extending slightly behind tip of bud (before opening).

(5) *Peduncle.*—Length — normal. Aspect — straight. Strength — erect. Color — 144A, with 53B overlay; 53B predominates in full sun.

B. Bloom:

(1) *Size.*—Average size when fully expanded-about $1\frac{3}{8}$ to $1\frac{1}{2}$ inch.

(2) *Borne.*—Primarily singly.

(3) *Form.*—High centered blooms, becoming flat upon opening, petals reflexed individually over entire margin as they mature.

(4) *Petalage.*—Number of petals under normal conditions — about 28 to 35, but can have up to 55 with heavy fertilization.

(5) *Color (during first 2 days).*—Inner petals at center of flower — 48C, 7D at base. Outer petals — 48A. Base of petals (point of attachment) — 7D. Reverse of petals — 52C. General tonality from a distance — coral pink.

(6) *Color change.*—As bloom ages — color softens to 52C and the general tonality becomes pinker with less orange tone.

C. Petals:

(1) *Texture.*—Thick.

(2) *Appearance.*—Inside — velvety: Outside — Satiny, smooth.

(3) *Form.*—Fan shaped.

(4) *Arrangement.*—Regularly arranged, shingle-like.

(5) *Petaloids in center.*—Medium to few.

(6) *Persistence.*—Drop off cleanly.

(7) *Fragrance.*—Slight.

(8) *Lasting quality.*—Long lasting on plant.

2. REPRODUCTIVE ORGANS

A. Stamens, filaments and anthers:
(1) *Arrangement.*—Regularly arranged around styles.
(2) *Color.*—14D.

B. Pollen: None observed.

C. Styles: Medium length, few.

D. Stigmas: Color — 8D.

E. Hips: None observed.

3. PLANT

A. Form: Upright, compact.

B. Growth: Vigorous, free branching. Height attained — 12 to 18 inches.

C. Foliage: Compound 5 to 7 leaflets.
(1) *Size.*—Medium.
(2) *Quantity.*—Abundant.
(3) *Color.*—New foliage: Upper side — 145A edged 185A. Under side — 185C. Old foliage: Upper side — 131A. Under side — 148C.
(4) *Shape.*—Oval, pointed.
(5) *Texture.*—Upper side — glossy. Under side — matte.
(6) *Edge.*—Serrated, more pronounced toward the tip.
(7) *Serration.*—Regular, relatively deep.
(8) *Leaf stem.*—Color — near to 137C. Under side — 137D.
(9) *Stipules.*—Medium, smooth.
(10) *Resistance to disease.*—Blackspot — normal. Mildew — normal.

D. Wood:
(1) *New wood.*—Color — near 146A. Bark — smooth.
(2) *Old wood.*—Color — 137B. Bark — smooth, but can roughen with age.

E. Thorns:
(1) *Thorns.*—Quantity: few. On laterals — few. Form — straight, thin needle-like. Length — medium. Color — 168D changing to 177A on aging. Position — irregular, usually midway between nodes.

I claim:

1. A new and distinct variety of rose plant of the miniature class, substantially as shown and described, characterized particularly by coral pink high centered, recurrent flowers of persistent coloring borne primarily singly to a stem, with reflexing petals folding individually along the entire margin as they mature and are long lasting on the plant.

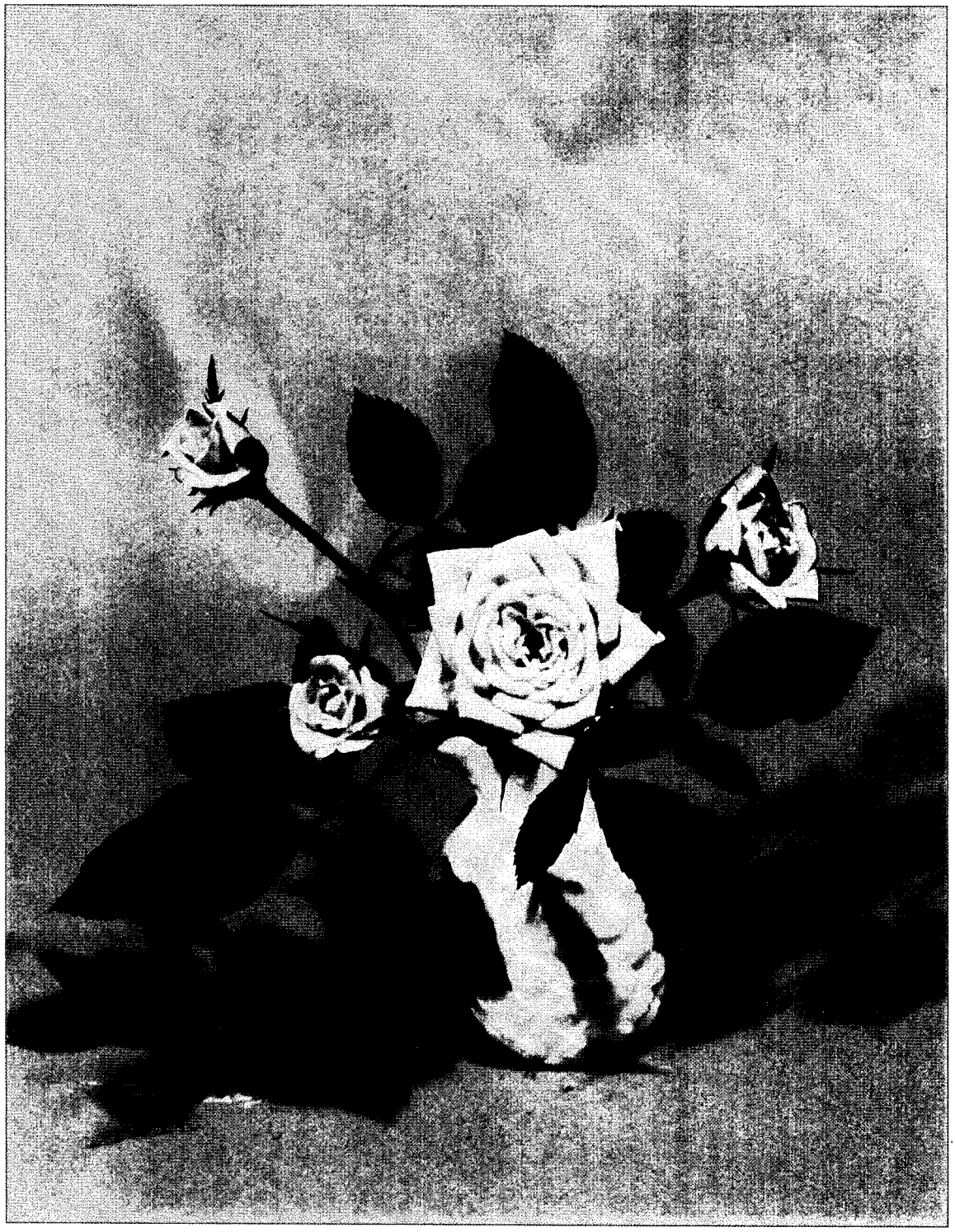

* * * * *